United States Patent [19]

Raaf et al.

[11] 4,169,885

[45] Oct. 2, 1979

[54] DENTAL AND ORAL HYGIENE PREPARATIONS

[75] Inventors: Helmut Raaf, Bad Schwalbach; Helmar R. Wagner, Darmstadt Arheilgen, both of Fed. Rep. of Germany

[73] Assignee: Blendax-Werke R. Schneider GmbH & Co., Postfach, Fed. Rep. of Germany

[21] Appl. No.: 886,469

[22] Filed: Mar. 14, 1978

[30] Foreign Application Priority Data

Mar. 19, 1977 [DE] Fed. Rep. of Germany ....... 2712161

[51] Int. Cl.$^2$ .......................... A61K 9/20; A61K 9/28; A61K 9/36; A61K 9/48
[52] U.S. Cl. ......................................... 424/16; 424/35; 424/37; 424/48; 424/49; 424/52; 424/57; 424/151
[58] Field of Search ..................................... 424/49–58, 424/16, 35, 48, 49, 151

[56] References Cited

U.S. PATENT DOCUMENTS

| | | | |
|---|---|---|---|
| 1,633,336 | 6/1927 | Larson | 424/49 |
| 2,004,957 | 6/1935 | Messner | 424/38 |
| 2,024,146 | 12/1935 | Crowther | 424/49 |
| 2,031,233 | 2/1936 | Stillwell | 424/49 |
| 2,089,845 | 8/1937 | Atkins | 424/49 |
| 2,778,045 | 1/1957 | Bly et al. | 424/49 |
| 3,431,339 | 3/1969 | Gyarmathy et al. | 424/57 |
| 3,475,533 | 10/1969 | Mayrand | 424/57 |
| 3,574,824 | 4/1971 | Echeandia et al. | 424/50 |
| 4,069,312 | 1/1978 | Mannara | 424/49 |
| 4,071,614 | 1/1978 | Grimm | 424/49 |

*Primary Examiner*—Shep K. Rose
*Attorney, Agent, or Firm*—Connolly and Hutz

[57] ABSTRACT

Disclosed is a dental hygiene preparation in the form of a filled capsule or a filled sweet comprising an outer shell containing a hydrophilic dental and/or oral hygiene substance and an inner core of a lipophilic substance.

8 Claims, No Drawings

DENTAL AND ORAL HYGIENE PREPARATIONS

FIELD OF THE INVENTION AND STATE OF THE ART

The present invention relates to a dental hygiene preparation for applying active substances such as fluorine compounds, antimicrobial agents, etc. to the surface of the teeth and for keeping them there for a relatively long period of time.

It has been known for a long time to add to dental hygiene preparations, such as tooth pastes and mouth washes, substances that are intended to have a prophylactic or therapeutic effect on the teeth and the gums and the mucous membrane of the mouth. Tooth pastes that contain various flourides as preventatives against caries have been on the market for a long time.

Dental hygiene preparations containing active substances that prevent or reduce the formation of dental plaque and/or tartar are also known. A considerable disadvantage of these active substances incorporated into conventional dental hygiene preparations is that only the relatively short time for which the teeth are being cleaned or the mouth is being rinsed is available for them to take effect, so that a substantial part of the total activity potential cannot be exploited.

SUMMARY OF THE INVENTION

It has now been found that these disadvantages may be overcome if a dental hygiene preparation is produced that is in the form of a capsule or filled sweet, a hydrophilic active dental and oral hygiene substance being contained in the outer shell of the capsule, while a lipophilic substance is contained inside the shell. The lipophilic substance is such that it tends to coat the teeth and gums when released into the mouth after the wall of the capsule has been worn away by the action of sucking and to overlie the hydrophilic substance thereby retaining it in contact with the teeth and gums. In this manner optimum use is made of the full activity of the hydrophilic active substances and an important contribution is made to preserving the health of the teeth and gums.

DETAILED DESCRIPTION OF THE INVENTION

The mode of operation of the preparations according to the invention thus consists in the hydrophilic active substance being gradually released from the wall of the capsule as the capsule or sweet is being consumed, and coating the teeth and gums. After the outer shell of the preparation according to the invention has been worn away, the hydrophilic active substance coating teeth and gums is fixed by the lipophilic active substance that is contained inside the preparation and released later than the hydrophilic substance.

Fluorine compounds that are suitable for the prevention of caries, are primarily suitable for consideration as hydrophilic active substances that are contained in the outer shell of the preparation according to the invention. Such fluorine compounds are, for example, fluorides such as sodium fluoride and potassium fluoride, tin fluoride, organic fluorides such as long-chained aminofluorides, for example oleylaminofluoride, cetylaminofluoride or ethanolaminohydrofluoride, fluorosilicates, for example potassium hexafluorosilicate or sodium hexafluorosilicate, fluorophosphates such as ammonium, sodium, potassium, magnesium or calcium monofluorophosphate and/or fluorozirconates, for example sodium, potassium or tin fluorozirconate.

The preferred proportion is between 0.05 and 1.0% by weight of fluoride, calculated as fluorine, of the shell or otherwise total composition.

Antimicrobial substances that can prevent or at least reduce the formation of dental plaque caused by bacteria may also, or alternatively be present in the shell of the capsule. Examples of such compounds are, in particular, 1,6-bis-(p-chlorophenyldiguanido)hexane, known by the trivial name "chlorhexidine", which may be used in the form of its water-soluble salts such as digluconate, diacetate, dilactate or also the less readily soluble dihydrochloride; 1,6-di-(2-ethylhexyldiguanide)hexane, known by the trivial name "alexidine", similarly in the form of its water-soluble salts; 1,6-di-(benzyldiguanido)-hexane, p-chlorophenyl-diguanide or $N^1$(4-chlorobenzyl)-$N^5$-(2,4-dichlorobenzyl)diguanide similarly in the form of their soluble salts; polymeric bis-guanides as sold, for example, under the trade name "Vantocil", and also other diguanides, for example those disclosed in U.S. Pat. No. 3,183,230. Quaternary ammonium compounds are also suitable hydrophilic antimicrobial substances which may be used in the preparations of the invention.

Preferably 0.01 to 2.5% by weight of the antimicrobial substances are used.

Another group of compounds which may be used in the shell of the preparations according to the invention comprises zinc compounds that are active in preventing dental plaque and tartar, such as zinc chloride, zinc phenolsulphonate, and zinc citrate, for example, in the form of its trihydrate, in a quantity between 0.01 and 2.5% by weight calculated as zinc, of the preparation according to the invention.

Tartar inhibiting substances may be used in the preparations of the invention especially, for example, the various phosphonic acids and their water-soluble salts, for example ethane-1-hydroxy-1,1-diphosphonic acid, ethylenediaminotetraphosphonic acid, hexamethylenediaminotetraphosphonic acid; complex-forming polycarboxylic acids, in particular citric acid and tartaric acid and their water-soluble salts. The proportion of such tartaric inhibiting substances may be 0.05 to 7.5% by weight of the preparation according to the invention.

The various cariostatically active water-soluble phosphates for example inorganic phosphates such as sodium trimetaphosphate, and organic phosphates, in particular phosphoric acid esters of polyhydric alcohols such as sodium or calcium glycerophosphate or calcium saccharose phosphate, may also be used as hydrophilic substances in the dental and oral hygiene preparations according to the invention, in the known suitable quantities.

Combinations of different odontologically active substances that are compatible with one another may also be used.

The following are examples of expecially suitable lipophilic substances, released only after the outer shell has been conxumed, that may be used for filling the capsule or sweet according to the invention: natural and synthetic fats and waxes, for example edible fats, mono- and diglycerides, carnauba wax, candelilla wax, spermaceti, bees-wax, synthetic esters of long-chained fatty acids, such as isopropyl myristate, isopropyl stearate or isopropyl palmitate; phospholipids, such as lecithin or cephalin, squalene or perhydrosqualene or synthetic substitutes for these; abietic acid and salts thereof; cholesterol, lanosterol; fatty alcohols such as carnaubyl alcohol, ceryl alcohol, miricyl alcohol, miristyl alcohol, isostearyl alcohol, oleyl ricinol, undecylic acid and the corresponding long-chained fatty acids, the lipophilic salts thereof, for example castor oil fatty acid and sodium ricinoleate, and the esters thereof; long-chained amines, such as cetylamine or stearylamine; peptides, lipoproteins and lipoproteic acids, for example of the "lipacid" type, and also various silicon oils.

The joint use of several lipophilic substances, if desired in solution, is also possible. The proportion of the lipophilic substances of the total composition is advantageously between 1 and 75%, but is preferably between 5 and 50% by weight.

The manufacture of the capsules or sweets according to the invention is effected in the customary manner, as described, for example, in Munzel-Buchi-Schultz, "Galenische Praktikum" (1959), Wissenschaftliche Verlagsgesellschaft mbH, Stuttgart, pages 501 to 505, or in Ullmanns Enzyklopadie der technische Chemie, 3rd edition, Vol. 4, pages 12 to 15 and Vol. 19, pages 257 to 258.

The following Examples provide a synopsis of dental and oral hygiene preparations combined according to the invention in capsule form or as filled sweets.

Filled gelatin capsules of the following composition were prepared in the customary manner:

EXAMPLE 1

| (a) Composition of the capsule shell | |
|---|---|
| gelatin | 460.0 mg |
| glycerin | 120.0 mg |
| sorbitol, 70% strength | 90.0 mg |
| peppermint oil | 3.0 mg |
| spearmint oil | 2.0 mg |
| saccharin sodium | 2.3 mg |
| sodium cyclamate | 15.0 mg |
| benzoic acid | 3.0 mg |
| titanium dioxide | 1.0 mg |
| blue food coloring 3 | 0.1 mg |
| yellow food coloring 2 | 0.1 mg |
| (b) Composition of the filling | |
| silicon oil | 400.0 mg |
| xylite | 700.0 mg |

EXAMPLE 2

| (a) Composition of the capsule shell | |
|---|---|
| gelatin | 520.0 mg |
| glycerin | 20.0 mg |
| sorbitol | 97.0 mg |
| chlorhexidinediacetate | 10.0 mg |
| peppermint oil | 2.5 mg |
| menthol | 2.3 mg |
| saccharin sodium | 1.0 mg |
| sodium cyclamate | 10.0 mg |
| sorbic acid | 5.0 mg |
| titanium dioxide | 2.0 mg |
| red food coloring 4 | 0.2 mg |
| (b) Composition of the filling | |
| sunflower oil | 900.0 mg |
| cetylamine | 100.0 mg |

EXAMPLE 3

| (a) Composition of the capsule shell | |
|---|---|
| gelatine | 500.0 mg |
| glycerin | 100.0 mg |
| sorbitol, 70% strength | 72.5 mg |
| sodium fluoride | 3.5 mg |
| peppermint oil | 3.0 mg |
| spearmint oil | 2.0 mg |
| saccharin sodium | 4.0 mg |
| p-hydroxybenzoic acid ester | 5.0 mg |
| titanium dioxide | 2.0 mg |
| chlorophyllin | 3.0 mg |
| sodium trimetaphosphate | 5.0 mg |
| (b) Composition of the filling | |
| mono- and diglycerides of coconut oil fatty acid | 300.0 mg |
| lecithin | 700.0 mg |

EXAMPLE 4

| (a) Composition of the capsule shell | |
|---|---|
| gelatine | 530.0 mg |
| glycerin | 70.0 mg |
| sorbitol, 70% strength | 69.4 mg |
| sodium monofluorophosphate | 7.5 mg |
| peppermint oil | 2.0 mg |
| spearmint oil | 2.0 mg |
| saccharin sodium | 7.0 mg |
| p-hydroxybenzoic acid ester | 3.0 mg |
| titanium dioxide | 2.0 mg |
| blue food coloring 3 | 0.1 mg |
| 1-hydroxyethane-1, 1-di-phosphonic acid | 5.0 mg |
| (b) Composition of the filling | |
| carnauba wax dissolved in | 300.0 mg |
| Miglyol 812 neutral oil | 600.0 mg |

EXAMPLE 5

A sucking tablet with a center was composed as follows:

| (a) Composition of the tablet shell | |
|---|---|
| sorbitol (e.g. Karion HF 3160 of the firm of Merck | 2,200.0 mg |
| dicalcium glycerophosphate | 200.0 mg |
| magnesium stearate | 23.0 mg |
| cetylbenzyldimethylammonium chloride | 3.0 mg |
| citric acid | 20.0 mg |
| peppermint essence | 3.0 mg |
| orange food coloring 2 | 1.0 mg |
| (b) Composition of the center | |
| sodium ricinoleate | 75.0 mg |
| sorbitol (e.g. Karion HF 3160 of the firm of Merck) | 100.0 mg |
| peppermint essence | 2.0 mg |
| polyethyleneglycol 6000 | 23.0 mg |

As the foregoing illustrates the shell material carrying the hydrophilic, odontologically active substance may be a known gelatine or candy-type base which is itself water soluble.

What we claim is:

1. A filled sucking tablet preparation for dental and oral hygiene comprising a water soluble candy-type based outer shell and an inner filling material, said shell containing a hydrophilic, odontologically active substance which is released as the shell is worn away in the mouth with said active substance being selected from the group consisting of a water soluble inorganic fluoride, an organic fluoride, a fluorosilicate, a zinc compound, a phosphoric acid, a complex-forming polycarboxylic acid, a water-soluble inorganic phosphate, a water-soluble phosphoric acid ester of a polyhydric alcohol, a water soluble antimicrobial agent, and mixtures thereof, and said inner filling material comprising a hydrophobic substance selected from the group consisting of natural fats and waxes, synthetic fats and waxes, phospholipids, abietic acid or a salt thereof, cholesterol, lanosterol, a fatty alcohol, a long chain fatty acid, lipophilic salts or esters of long chain fatty acids, a long chain amine, a peptide, a lipoprotein, a lipoproteic acid, a silicone oil, and mixtures thereof.

2. The preparation according to claim 1 wherein the amount of fluorine compound calculated as fluorine is 0.05 to 1.0% by weight of the total composition.

3. The preparation according to claim 1 wherein the hydrophilic, odontologically active substance is a water-soluble anti-microbial agent selected from the group consisting of a water-soluble salt of chlorhexidine, a water-soluble salt of alexidine, a quaternary ammonium compound, a monomeric or polymeric diguanide and mixtures thereof.

4. The preparation according to claim 3 wherein the amount of anti-microbial agents is 0.01 to 2.5% by weight of the total composition.

5. The preparation according to claim 1 wherein the hydrophilic, odontologically active substance is a zinc compound selected from the group consisting of zinc chloride, zinc citrate and zinc phenol sulphonate.

6. The preparation according to claim 1 wherein the inner filling material within the shell is a lipophilic substance selected from the group consisting of an edible fat, a monoglyceride, a di-glyceride, carnauba wax, candelilla wax, spermaceti, bees wax, isopropyl myristate, isopropyl stearate or isopropyl palmitate, lecithin, cephalin, squalene, perhydrosqualene, carnaubyl alcohol, ceryl alcohol miricyl alcohol, miristyl alcohol, isostearyl alcohol, oleyl ricinol, undecylic acid, castor oil, fatty acid, cetyl amine, stearylamine and mixtures thereof.

7. The preparation according to claim 1 wherein the inner filling material within the shell is sodium ricinoleate.

8. The preparation according to claim 1 wherein the lipophilic substance comprises 1 to 75% by weight of the total composition.

* * * * *